United States Patent [19]

Nowacki et al.

[11] Patent Number: 4,905,674

[45] Date of Patent: Mar. 6, 1990

[54] ELECTRODE CONSTRUCTION FOR REPLACEMENT OF WORN ELECTRODES IN A LITHOTRIPTER

[75] Inventors: Christopher Nowacki, Long Grove; Alfred G. Brisson, Kildeer; Exequiel D. Cruz, Arlington Heights, all of Ill.

[73] Assignee: Northgate Research, Inc., Arlington Heights, Ill.

[21] Appl. No.: 278,369

[22] Filed: Dec. 1, 1988

[51] Int. Cl.⁴ .............................................. A61B 17/22

[52] U.S. Cl. .................................................. 128/24 A

[58] Field of Search ................ 128/328, 24 A, 660.03; 367/142, 147; 181/142, 402; 313/140, 602; 362/210; 123/169, 169 EA, 169 EB, 169 EC, 169 EL; 314/130; 219/383, 384

[56] References Cited

U.S. PATENT DOCUMENTS

| | | | |
|---|---|---|---|
| 591,783 | 10/1897 | McClellan | 219/383 |
| 3,783,237 | 1/1974 | McArthur | 219/384 |
| 4,730,614 | 3/1988 | Lacruche et al. | 128/328 S |

FOREIGN PATENT DOCUMENTS

| | | | |
|---|---|---|---|
| 0148021 | 9/1982 | Japan | 123/169 EL |

*Primary Examiner*—Kyle L. Howell
*Assistant Examiner*—K. M. Pfaffle
*Attorney, Agent, or Firm*—Robert M. Wolters

[57] ABSTRACT

An electrode construction is provided for electrohydraulic shock wave generation such as for extracorporeal kidney stone destruction. The construction includes a reflector adapted to be filled with liquid such as water for coupling to a human body. The reflector has a focus point. An insulated base supports a plurality of pairs of electrodes, and is movable relative to the reflector. The insulating base is moved to bring successive pairs of electrodes into substantial coincidence with the focus point of the reflector. Upon such movement electrical connection is automatically made to extensions of the pair of electrodes having their spark gap substantially coincident with said focus point.

9 Claims, 2 Drawing Sheets

48
14
16
10
12
28
36
32
26
22
20
20
32
24
42
42
18
38
34
44
44
30
SPARK GEN.
46

52
42''
32
26
24
42'
20''
20'
42
22
42
20
20
42'
20'
20''
42''
40

62
58
62
42
60
60
54
60
56
58
60

ELECTRODE CONSTRUCTION FOR REPLACEMENT OF WORN ELECTRODES IN A LITHOTRIPTER

BACKGROUND OF THE INVENTION

Surgery for kidney stones is traumatic, generally for the patient, and specifically for the kidney. There is a recuperation period of 6 to 12 months, and the number of surgical operations on a kidney is quite limited, generally on the order of three. After this time the kidney has a great deal of scar tissue, and is traumatized to the point where it simply ceases to function.

Lithotripters for the extracorporeal destruction of kidney stones are known, and such operations in most cases can in a finite period of time reduce a kidney stone to wet dust which is passed out with the urine. This is true whether the kidney stone is actually in the kidney, or is in the bladder, or in the ureter between the kidney and the bladder. Lithotripters generally comprise a truncated ellipsoidal reflector. The reflector is filled with a liquid, commonly water, which couples the interior of the reflector to a human body, and through the tissues of the body to the kidney stone. The reflector is provided with a spark gap at the first focus point of the ellipsoid. The ellipsoidal reflector is positioned relative to the human body so that the second focus point of the ellipsoid lies on the kidney stone. A spark across the spark gap causes a certain amount of water to be flashed into steam, accompanied with generation of a shock wave. This shock wave is focused by the ellipsoidal reflector on the second focus point, and hence on the kidney stone. A fairly rapid succession of such sparks over a period of up to an hour is sufficient to disintegrate substantially any kidney stone, whereby the kidney stone is disintegrated, and subsequentally flushed out with the urine, without the necessity of in any way invading the body. A patient can generally go home the day following such treatment.

The electrodes forming the spark gap often are made of brass. Sometimes the confronting tips of the electrodes are made of tungsten, and a combination of brass on one electrode and tungsten on another is also known. Regardless of the material the service life of a pair of electrodes is quite limited. High electric power is dissipated in each spark, and the result is that the electrodes become vaporized, pitted and worn away. It is therefore necessary to replace electrodes frequently. Considerable time is required to replace a pair of electrodes in accordance with known practice. This can occur one or more times during treatment of a patient, and a delay is detrimental to the state of mind of the patient, particularly in instances in which the patient is suspended with the ellipsoidal reflector in a water bath.

OBJECTS AND SUMMARY OF THE PRESENT INVENTION

In view of the foregoing it is an object of the present invention to provide an electrode construction in a lithotripter wherein electrodes are easily and quickly replaced.

More particularly, it is an object of the present invention to provide a plurality of pairs of electrodes in a lithotripter, wherein successive pairs of electrodes are readily shifted into position to replace the electrodes as they erode or dissipate.

It is further an object of the present invention to provide replaceable electrodes in a lithotripter wherein electrical connections are made automatically as one set of electrodes substitutes for another.

In carrying out the foregoing and other objects of the present invention a lithotripter is provided with a holder for a plurality of sets of electrodes, which holder is readily movable to shift successive pairs of electrodes into position to form a spark gap at the first focus point of the lithotripter, and wherein the electrodes automatically become associated with electrical contacts upon being so shifted. The electrodes are mounted and are shiftable in an insulating base which may be in the form of a doughnut like ring which is rotatable to position pairs of electrodes at the first focus point of the ellipsoidal reflector, and simultaneously to bring fresh electrodes automatically into contacting engagement with electrical connectors. Alternatively, the insulating base carrying the electrodes may be in the form of a plug which is axially shiftable in the reflector to bring axially spaced pairs of electrodes successively into operative position at the first focus point of the reflector. The electrodes automatically come into contact with suitable electrical contacts to effect the requisite energization of the electrodes.

THE DRAWINGS

The present invention will best be understood with reference to the following specification when taken in connection with the accompanying drawings wherein.

DETAILED DESCRIPTION OF THE ILLUSTRATED EMBODIMENT

Figure 1:
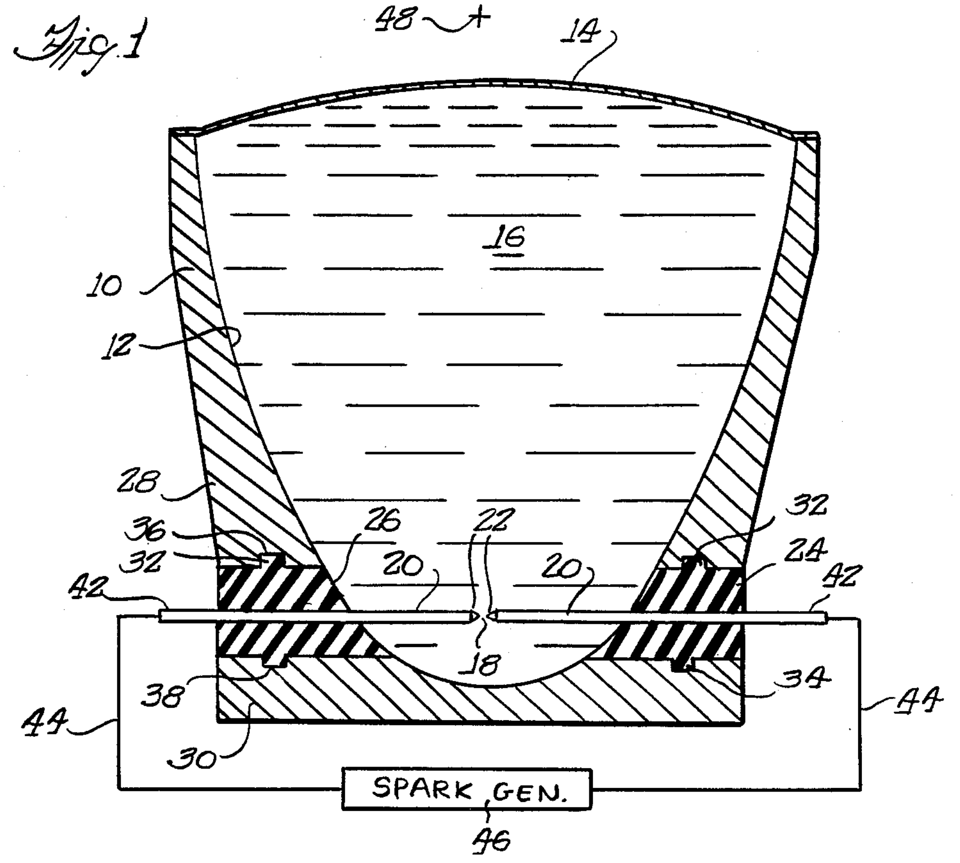
FIG. 1 is an axial sectional view of an apparatus embodying an electrode construction for electrode hydraulic shock wave generation in a lithotripter.

Turning now to the figures of the drawings in greater particularity first to FIG. 1, there will be seen a portion of a lithotripter comprising a reflector bowl or the like 10 having an interior surface 12 comprising a portion of an ellipsoid of revolution. The major axis of the ellipsoid is shown as being vertical, but it will be understood that the reflector can be tipped. The top of the reflector is closed by a flexible diaphragm 14 to be pressed against the body of a human patient, and the interior of the reflector is filled with a liquid such as water 16. Near the bottom of the reflector, and specifically at the first focus point 18 thereof are a pair of electrodes 20 defining a spark gap 22. The electrodes commonly are made of brass, or could be tungsten or could be a combination of tungsten and brass, such as one electrode brass and one tungsten, tungsten tips, or plating over brass. The electrodes are mounted in confronting relation by means of a ring 24, the inner surface 26 of which comprises a continuation of the ellipsoidal surface 12. The ring 24 must be of electrically insulating material to provide electrical isolation of the electrodes 20, and it must be strong and dimensionally stable. One preferred substance for this ring is a glass-filled epoxy. The bowl 10 may be made of a suitable metal, or of a plastic material such as the glass filled epoxy noted for the ring 24.

The ring is mounted between an upper portion 28 of the bowl 10 and a lower portion or base 30 thereof, and may have an upstanding annular rib 32 and a depending annular rib 34 received in corresponding recessed rings or channels 36 and 38 in the upper portion 28 and the base 30, respectively. The ring is thereby connected to the reflector 10 in such manner that it cannot shift laterally yet can be readily rotated such as by means of a radially extending handle 40 shown in FIG. 2.

Figure 2:
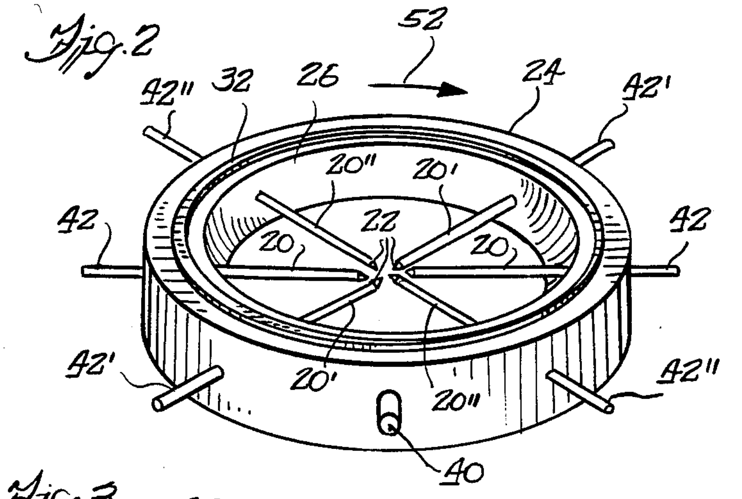
FIG. 2 is a perspective view of the electrode construction of FIG. 1, shown removed from the ellipsoidal reflector for clarity of illustration.

Additional pairs of electrodes, illustrated in FIG. 2 at 20' and 20'' are mounted by the ring 24 in angularly spaced relation. In the specific example of three sets of electrodes as shown in FIG. 2, the spacing between sets or pairs of electrodes is 60°. Each pair of electrodes defines a spark gap. Each electrode such as the electrodes 20 has an integral outer end extending radially out beyond the ring 24, as shown at 42, 42' and 42''. One pair of electrodes at a time is connected by means such as electrical conductors 44 to an electrical spark generator 46 as shown in FIG. 1.

A spark generated by the spark generator 46 and jumping across the spark gap 22 causes a certain amount of water to flash into steam, and effects generation of a shock wave which is reflected from the first focus point 18 of the reflector 12 to the second focus point 48 of the reflector, the second focus point being shown somewhat below its actual position in FIG. 1 for drawing convenience. As is known, the diaphragm 14 is pressed against the body of a human patient in such manner that the second focus point 48 lies on a kidney stone to be disintegrated. Repeated shock waves over a period of time up to about an hour will reduce the offending kidney stone to small fragments or dust which are passed out with the urine.

Figure 3:
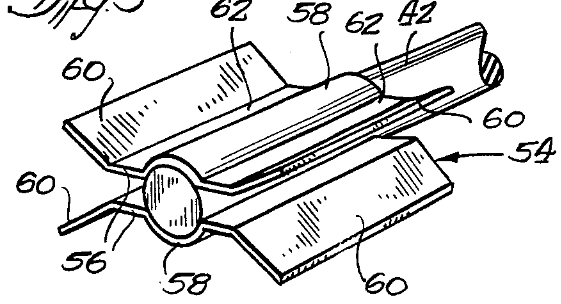
FIG. 3 is an enlarged and exploded perspective view of engagement of one electrode with an electrical contacting device or jack.
Figure 4:
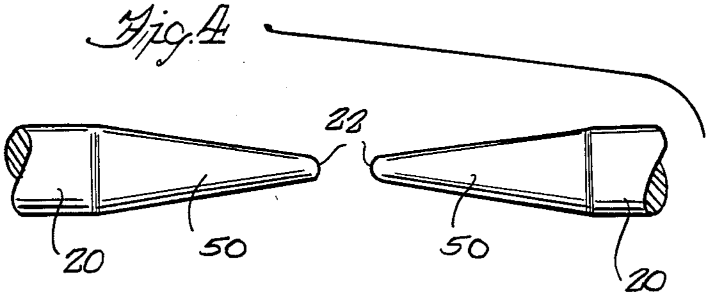
FIG. 4 is a view on an enlarged scale showing the confronting portions of a pair of electrodes, taken substantially transversely of the pair of electrodes.
Figure 5:
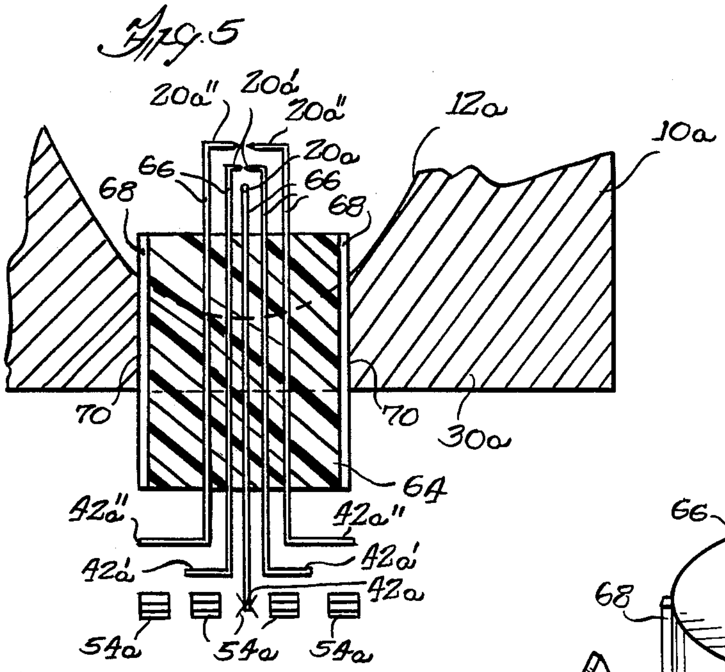
FIG. 5 is a fragmentary view generally similar to a portion of FIG. 1 showing a modification of the present invention.

The confronting tips 50 of the electrodes 20 defining the spark gap 22 are initially conical in shape, as shown in FIG. 5, and specifically with hemispherical extremities. Repeated sparks across the gap cause erosion and deterioration causing the tips to become of irregular shape, progressively to be spaced a greater distance apart. This results in an inferior spark, and a reduced intensity shock wave. Eventually, the spacing, and the irregular nature of the tips, combined with oxidation or corrosion of the tips causes the spark to be weak and the shock wave generated to be correspondly weak, to a point where it becomes necessary to replace the electrodes. In accordance with conventional practice a rather thorough disassembly has been required, with reassembly involving fresh electrodes. However, in accordance with the present invention it is only necessary to rotate the ring 24 by 60° to bring a fresh pair of electrodes into operating position. Simultaneously, electrical contact with the initial pair of electrodes is interrupted, and contact is made with the fresh pair of electrodes by means of structures such as that shown in FIG. 2. Specifically, electrical contact with the projecting end of each pair of electrodes is effected by means of a spring clip 54 as shown in FIG. 3. The clip is mounted from suitable insulating means (not shown), and includes a pair of contacting leaves 56 which may be biased toward one another by their resilient, insulating mount, or which may be integral to the left of the leaves that are shown in FIG. 3. Each leaf is substantially rectangular in outline, and comprises a central trough-like portion 58, opposing trough-like portions gripping the extending end 42 of the electrode 20. As will be understood the trough-like portions are oriented radially of the ring 24, but are fixed, so that they remain in the same position as the ring rotates. Outer flanges 60 of the leaves are arranged in diverging pairs, secured to the central trough-like portions 58 by spacer portions 62. As will be apparent, the outwardly projecting end 42 of one electrode 20 cams its way out of the spring clip 54 as the ring 24 is rotated, the outer end of the next electrode 20' thereafter camming into place between the leaves 56 of the spring clip 54. As will be understood, there are two such contacts or connectors, and these are respectively connected to the wires 44 leading to the spark generator 46. It will thus be seen that when the tips of one pair of electrodes become so eroded and deteriorated as to require replacement, it is only necessary to shut off the spark generator momentarily, and to rotate the ring 24 through a 60° arc to bring a succeeding pair of fresh electrodes into position, simultaneously effecting electrical engagement of the outer ends of the new pair of electrodes with the electrical contactors or connectors. Thus, the time to replace electrodes is measured in a matter of seconds or a very few minutes, as contrasted with the many minutes heretofore required. Although three pairs of electrodes are shown in the illustration, it will be appreciated that there could be as few as two pair, or that there could be a number of pairs greater than three.

Figure 6:
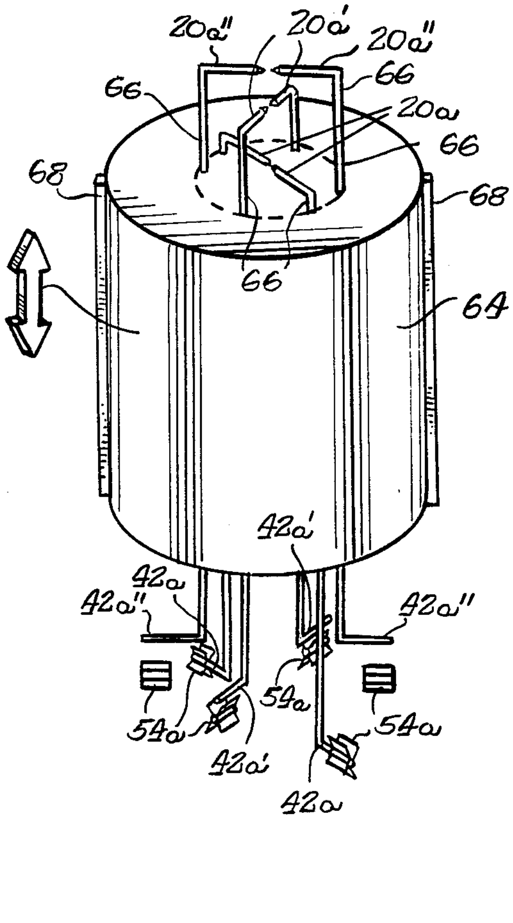
FIG. 6 is a perspective view of the electrode construction of FIG. 5.

A modification of the invention is shown FIGS. 5 and 6. In this embodiment similar parts are identified by like numerals with the addition of the suffix a. In the present embodiment the three pairs of electrodes 20*a*, 20*a*', 20*a*'' illustrated are secured in an insulating axially mounted plug or cylinder 64. This cylinder preferably comprises a glass fiber reinforced epoxy. The three pairs of electrodes are spaced at 60° and are also spaced vertically, being mounted by means of vertical rods 66 extending through the cylinder 64 and above and below the cylinder. The rods and electrodes, including electrode extensions 42*a* and the electrical connectors or contactors 54*a* are shown in quasi-planar arrangement in FIG. 5 for simplicity of illustration, and it is comtemplated that the rods and electrodes could actually be so mounted. However, the angular arrangement shown more definitely in FIG. 6 is preferred for convenience of disposition of the electrodes and for electrical isolation. Since the electrodes 20*a* and the extensions 42*a* thereof are spaced angularly as well as vertically, there are three pairs of electrical contactors or connectors 54*a*, arranged in a common plane, but angularly spaced.

Initially the plug or cylinder is so positioned as to place the first set of electrodes 20*a* at the first focus point of the reflector 12*a*. When this set of electrodes has become eroded and otherwise worn out, the plug is simply moved down a short distance to bring the second pair of electrodes 20*a* into position. This is subsequently repeated to bring the third set of electrodes 20*a*'' into position. As will be understood, more than three pair of electrodes or only two pairs of electrodes could be used, rather than the three illustrated. The cylinder may be non-rotatably keyed to the body comprising the reflector by means such as longitudinally extending ribs 68 on the cylinder 64 and cooperating channels 70 in the reflector bowl 10*a*.

In both embodiments of the invention as illustrated the electrodes and extensions may be molded into the ring or cylinder with the insulating carrier and electrodes being replaceable as a unit when all of the electrodes are worn out. Alternatively, means can be provided for replacing the electrodes in the insulating base, although the molded-in structure is preferred as presenting less field service problems. As noted, the base, either the ring or the cylinder, is preferably a glass ring or fiber reinforced epoxy molding. The reflector bowl 10 including the interior surface 12 preferably is made of brass, although other materials may be used.

The specific example of the invention as herein shown and described is for illustrative purposes only. Various changes in structure will no doubt occur to those skilled in the art, and will be understood as forming a part of the present invention insofar as they fall within the spirit and scope of the appended claims.

The invention here is claimed as follows:

1. An apparatus for use in electrohydraulic shock wave generation comprising a reflector adapted to be filled with a liquid such as water, said reflector having a focus point, insulating base means mounted in and movable relative to said reflector, a plurality of pairs of electrodes carried by said insulating base means, each pair of electrodes being in spaced confronting relation defining a spark gap, said insulating base means being movable relative to said reflector to position said respective pairs of electrodes sequentially, said spark gaps of each said respective pair being substantially coincident with said focus point, and means for sequentially effecting electrical connection to a pair of said electrodes for generating a spark across said gap.

2. The apparatus as set forth in claim 1 wherein said electrodes are elongated transversely of a longitudinal axis of said reflector, and each pair of electrodes is axially aligned.

3. The apparatus as set forth in claim 1 wherein successive pairs of electrodes are spaced angularly.

4. The apparatus as set forth in claim 1 wherein said insulating base means comprises a ring and wherein said pairs of electrodes extend radially through said ring, successive pairs of electrodes being angularly spaced in said ring.

5. The apparatus as set forth in claim 4 and further including for rotating said ring relative to said reflector.

6. The apparatus as set forth in claim 5 and further including a plurality of extensions respectively from said pairs of electrodes extending outwardly of said ring, said means for effecting electrical connection to said electrodes comprising a pair of electrical contacts successively engaged by pairs of said extensions upon rotation of said ring.

7. The apparatus as set forth in claim 1 wherein said insulating base means comprises a member movably mounted in said reflector means for movement along a longitudinal axis thereof.

8. The apparatus as set forth in claim 7 wherein pairs of electrodes are spaced along said longitudinal axis relative to other pairs of electrodes.

9. The apparatus as set forth in claim 8 and further including extensions respectively connected to said electrodes, pairs of extensions being spaced along said longitudinal axis, said means for effecting electrical connection comprising at least one pair of electrical contacts selectively engageable with said extensions upon axial movement of said member.

* * * * *